United States Patent [19]

Donnelly

[11] 4,338,946

[45] Jul. 13, 1982

[54] VERSATILE POST MASTECTOMY DEVICE

[76] Inventor: Alice S. Donnelly, 24231 W. Trevino Dr., Valencia, Calif. 91355

[21] Appl. No.: 221,342

[22] Filed: Dec. 29, 1980

[51] Int. Cl.³ .......................... A41C 3/10; A41C 3/00
[52] U.S. Cl. .................................... 128/481; 128/488; 128/509; 128/483
[58] Field of Search ............... 128/488, 481, 452, 510, 128/509, 478, 479

[56] References Cited

U.S. PATENT DOCUMENTS 3,094,125  6/1963  Lewis ................................. 128/488
4,269,191  5/1981  Evans ................................. 128/488

*Primary Examiner*—Doris L. Troutman
*Attorney, Agent, or Firm*—Cislo, O'Reilly & Thomas

[57] ABSTRACT

In surgical procedures of the mastectomy and partial mastectomy type, a serious aftermath problem exists because of the present cultural attitude of such surgery. Authorities recognize the emotional trauma that a woman goes through after having been subjected to a radical, or less than radical, mastectomy. The removal of a woman's breast can have traumatic consequences and during the post operative stage, a need for femininity and a need for some means of reducing trauma is necessary. With the herein disclosed invention, a cover pad or the like, of aesthetic and feminine design, is disclosed which aids the woman in the post operative stage in a most positive and productive manner, especially with regard to her dealings with herself and those of a personal nature with others close to the wearer of the inventive device. A conformable fabric material covering of a variety of shapes is provided wherein a singular retaining means is provided wherein a plurality of loops may be utilized to receive a securement member in selected manner so that the device may be utilized in right hand or left hand manner and securely positioned about the body of the wearer.

8 Claims, 7 Drawing Figures

VERSATILE POST MASTECTOMY DEVICE

BACKGROUND OF THE INVENTION

Mastectomy and radical mastectomy procedures can be devastating to a woman from not only the physical standpoint, but from the emotional standpoint. Medical authorities are well aware of the psychological impact upon a woman who has undergone breast surgery. In order to reduce the impact of that surgery upon her and those around her, the device of the invention provides a cover, or the like, for the surgical situs which is of unique and selected configuration and design and of aesthetic quality so as to not only cover the surgical site of the mastectomy, or other surgery, but to impart psychological support to the wearer of the device, not only in her own mind, but also to present a pleasing appearance to those closely and personally associated with her.

While the prior art has suggested prosthesis devices, and the like, normally combined with other wearing apparel, as far as is known, no prior art device has suggested the unique device of the invention which is configured so that it may be used for covering left or right side surgical sites. Additionally, the device of the invention is such that it lends itself for whimsey and lighthearted approaches to otherwise serious physical and emotional matters.

OBJECTS AND SUMMARY OF THE INVENTION

It is an object of the invention to provide a post surgical device for covering surgical sites on a human body.

It is another important object of the invention to provide a versatile post mastectomy device which may be positioned on the right, left hand or both sides of a human body.

It is another, even more specific, important object of the invention to provide a post mastectomy device which is of aesthetic and unique configuration to aid in the emotional and physical trauma of a recovering patient.

It is another, even more important specific object of the invention to provide a versatile post mastectomy device, or the like, which is uniquely configured and of aesthetic pleasing appearance wherein the device is of conformable material and acts to protect the surgical site and to uplift the spirits of the wearer of same.

It is another, even further more specific object of the invention to provide a post surgical device of selected design and configuration wherein the device may be easily positioned and secured on the body of a wearer thereof, and wherein the device provides some limited physical protection to the sensitivity of the surgical site and also aids the emotional well-being of the wearer thereof.

In an exemplary embodiment, the invention pertains to a post surgical device for covering the surgical situs on a human body, comprising the combination of a cover member of selected configuration and ornamentation and being of a size sufficient to cover the surgical situs, wherein a plurality of spaced retaining means on the surface of the cover member adapted to overlie the surgical site, is provided for cooperative association with a securement member to secure same on the human body. A securement member is releasably received in the spaced retaining members and is of sufficient size to encircle, in adjustable fashion and supportive relationship, the cover member on the human body.

DESCRIPTION OF THE BEST EMBODIMENT CONTEMPLATED

Figure 1:
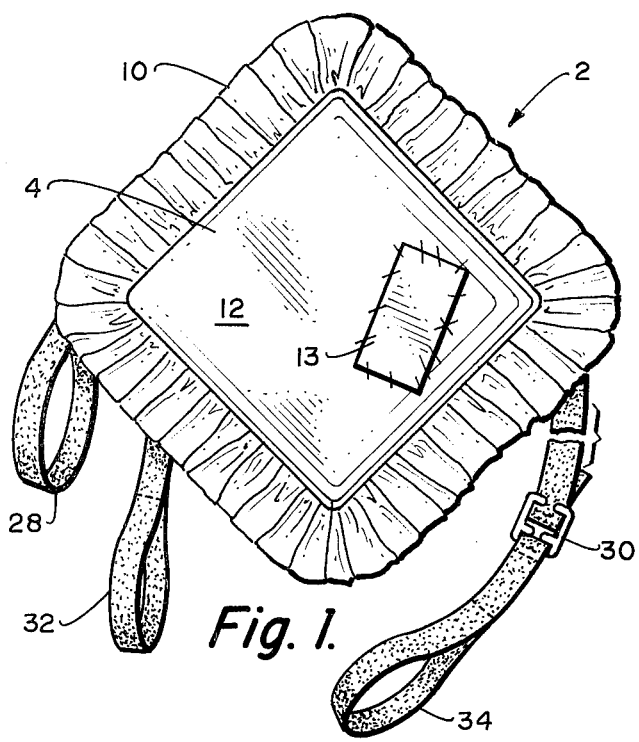
FIG. 1 is a front view of the post surgical device of the invention illustrating but one design and ornamentation.
Figure 4:
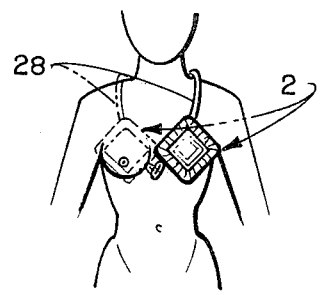
FIGS. 4-7 inclusive, are illustrative and schematic illustrations showing how the device of the invention may be utilized.
Figure 5:
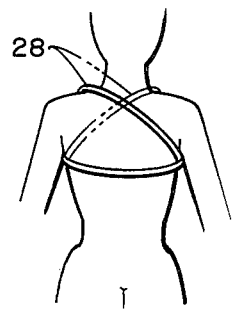
Figure 2:
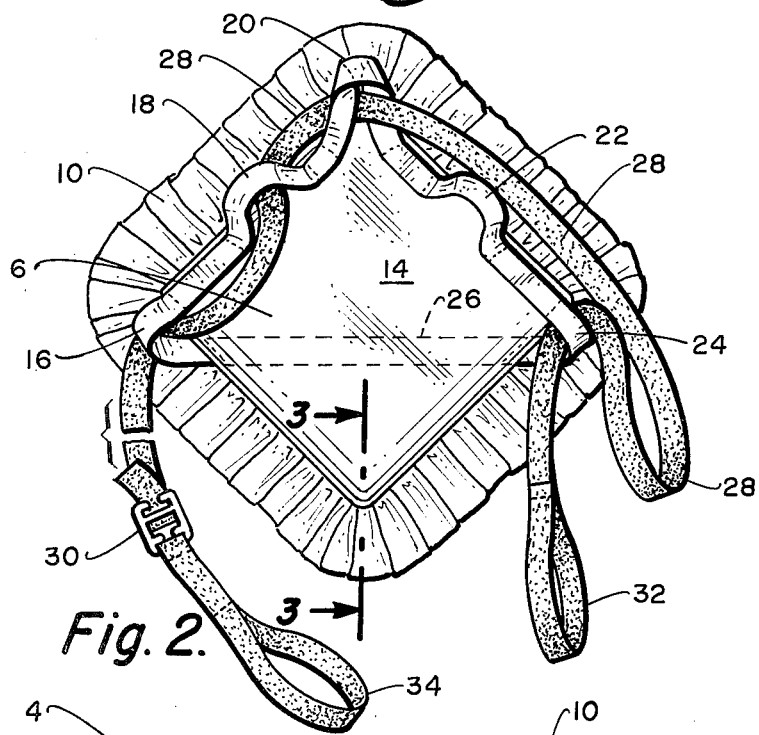
FIG. 2 is a back view of the device illustrated in FIG. 1.
Figure 6:
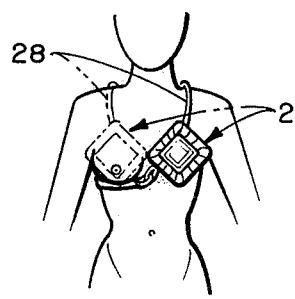
Figure 7:
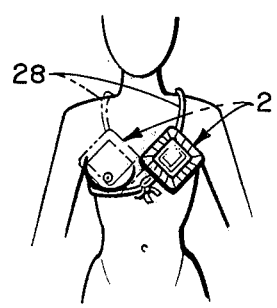
Figure 3:
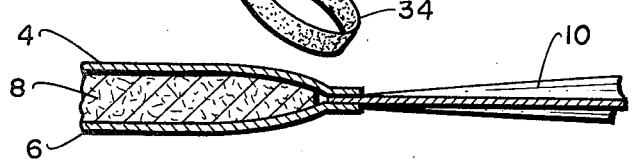
FIG. 3 is a fragmented view taken along the line 3—3 of FIG. 2.

Referring to FIGS. 1-3 inclusive, there is illustrated a post surgical device illustrative of the inventive concept herein, wherein the device may be of various designs and configurations, whether they be hearts, flowers, or the like, and wherein the materials of construction of the device may be such so as to provide some measure of physical protection for the mastectomy situs. It is to be understood that the ornamentation and the overall configuration of the device of the invention, as illustrated in the drawings and as more fully expounded upon in the hereinafter following commentary, are for illustrative purposes only. Those of ordinary skill in the art will at once recognize that various modifications and changes may be made to the overall configuration of the device of the invention without detracting from the essence of same.

Referring to the figures, the post surgical device 2 is illustrated in this exemplary embodiment as comprising two pieces, or segments, of cloth 4 and 6 of general rectangular configuration, having padding or other stuffing material 8 of conformable, pliable nature and terminating in ruffle-like perimetric portion 10 so as to provide a uniquely aesthetic, whimsical design. For example, the top surface or portion 12 may have attached a patch such as 13 for versatility and it is to be understood that other attachments or collages are possible, such as flowers and the like.

The rear or back surface 14 adapted to overlie the surgical site as would be found in a mastectomy, or the like, is provided with a plurality of spaced retaining means here taking the form of spaced loops 16 through 24, inclusive, and in this particular instance, being formed by a single elongated length 26 of twill tape, or the like, and being secured to the back surface 14 by any suitable means. The twill tape may be adhesively secured, or in the preferred embodiment, sewn to the member 2 where that member is comprised of fabric components.

It will be noted that loops 16, 20 and 24 form a triangle should a line be drawn therebetween, and there is provided intermediate loops 18 and 22 in the two legs of the substantially isosceles triangle formed by the line connecting the loops 16, 20 and 24.

For ease of construction and for washability, it is preferred that the device 2, as well as the retaining members, be made of cloth which is washable and colorfast, but it will be obvious that other retaining means may be utilized other than the specific twill tape, or segment 26 described and illustrated.

Intertwined through at least the loops 16, 20 and 24 is a segment of ribbon or tape 28 of either elastic or nonelastic construction and being of relative thinness and of a length to be able to encompass that portion of the human body as is necessary to adequately support the member 2 in encircling retained position as will be seen. So as to make the tape or ribbon 28 adjustable it is also provided with the usual adjustable buckle 30 so as to make the tape or ribbon 28 adjustable to either shorten or lengthen the same for comfortable wearing of the device 2 about the human body. There is no inventive claim to the buckle 30 and thus, no further description will be delved thereinto.

Referring to the illustrations in FIGS. 4–7, inclusive, there is shown in full line the device 2 positioned on a female who has had a mastectomy on the left side. Thus, the device 2 as illustrated, may be positioned in the manner shown in the full line drawings of FIGS. 4–7 inclusive, by reason of the tape or ribbon 28 being looped or threaded through the loops 16, 20 and 24. The ends 32 and 34 of tape or ribbon segment 28, may be either tied or otherwise secured together. For example, a plastic hook may be secured (not shown) in order to obtain the securement.

Whereas in the full line showing the tape segment 28 is intertwined through loops 16, 18, 20, and 24, for right side placement as shown in the dotted lines, the tape segments 28 would be threaded through loops 16, 20, 22, and 24 and positioned as shown in the dotted line illustrations of FIGS. 4–7 inclusive.

If it is desired and where a dual or bi-lateral mastectomy has been performed, the devices 2 may be joined together by placing two of like devices in side-by-side relationship and tying adjacent loops together and then intertwining the tape segment through the formed loops in a manner that will encompass, in supportive retained relationship, the peripheral edges of the members 2 for encircling engagement about the body of the wearer.

In some instances, it may be desirable to have the cover or patch 2 in secured relationship to the tape segment 28 as opposed to the loosely associated or releasable engagement as illustrated in FIGS. 1 and 2. In such instance, the tape segment 28 may be knotted at each of the retaining loops so as to hold the member 2 in secured fashion.

Thus, there has been disclosed a unique and versatile post mastectomy device which lends itself to a myriad of uses and design configurations and wherein the same may be used singularly or in side-by-side relationship depending upon the needs of the user. The device may be positioned on right or left hand body portions and various changes and modifications will suggest themselves to those of ordinary skill in the art and all of such modifications and changes will not depart from the essence of the invention and all such modifications and changes are intended to be covered by the appended claims.

I claim:

1. A post surgical device for covering the surgical situs on a human body comprising the combination of:
    a cover member of selected configuration and ornamentation and being of a size sufficient to cover said surgical situs;
    a plurality of spaced retaining means on the surface of said cover member adapted to overlie said surgical situs for cooperative association with a securement member to secure same on said human body; and
    a securement member releasably received in said spaced retaining means and being of sufficient size to encircle, in adjustable fashion and supportive relationship said cover member on said human body.

2. The device in accordance with claim 1 wherein said retaining means comprises an elongate member immovably secured about said surface and forming at least a plurality of spaced loops.

3. The device in accordance with claim 2 wherein said cover member is of conformable, flexible material and at least three spaced loops are provided.

4. The device in accordance with claim 3, wherein a line drawn between said three spaced loops forms a triangle.

5. The device in accordance with claim 4, wherein said cover member is of cloth having a soft fill and said elongate member is sewn to said cover member, and additionally forms two intermediate loops for selected reception of said securement member for right or left hand placement on said body.

6. The device in accordance with claim 5, wherein said securement member is provided with a buckle arrangement to permit elongation and shortening of said member.

7. The device in accordance with claim 6, wherein said elongate member is twill tape.

8. The device in accordance with claim 7, wherein said twill tape is knotted at said loops to prevent movement therebetween.

* * * * *